US00PP18151P3

(12) United States Plant Patent
NeSmith et al.

(10) Patent No.: US PP18,151 P3
(45) Date of Patent: Oct. 30, 2007

(54) SOUTHERN HIGHBUSH BLUEBERRY PLANT NAMED 'CAMELLIA'

(50) Latin Name: ***Vaccinium* sp. *hybrida***
Varietal Denomination: Camellia

(75) Inventors: D. Scott NeSmith, Molena, GA (US); Arlen D. Draper, Payson, AZ (US)

(73) Assignees: University of Georgia Research Foundation, Inc., Athens, GA (US); The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 11/282,299

(22) Filed: Nov. 18, 2005

(65) Prior Publication Data

US 2007/0118942 P1 May 24, 2007

(51) Int. Cl.
*A01H 5/00* (2006.01)

(52) U.S. Cl. ..... Plt./157

(58) Field of Classification Search ..... Plt./157
See application file for complete search history.

*Primary Examiner*—Kent Bell
(74) *Attorney, Agent, or Firm*—Greenlee Winner and Sullivan PC

(57) ABSTRACT

The most distinctive feature of the southern highbush blueberry, 'Camellia', is its combination of excellent fruit attributes, especially size and color, its relatively late flowering for a mid- to early-season variety and its excellent plant vigor under field and high density growth conditions.

4 Drawing Sheets

Botanical classification: *Vaccinium* sp. *hybrida.*
Varietal denomination: 'Camellia'.

ACKNOWLEDGEMENT OF FEDERAL RESEARCH SUPPORT

The invention was made in part with Federal funds pursuant to the Hatch Act.

BACKGROUND OF THE INVENTION

'Camellia' was selected in 1996 at the Coastal Plain Experiment Station in Tifton, Ga. from a cross of MS-122 ×MS-6. MS-122 was the female parent and MS-6 was the male parent. MS-122 is a propeny from across of G-144 ×US-121, and MS-6 is from a cross of G-107 x 'Sharpblue' (non patented). The numbered parents are breeding lines which are no longer available. These were never released or otherwise utilized because of inferior fruit quality and/or plant vigor. 'Camellia' a hybrid containing mostly *V. corymbosum* with a small amount of *V. darrowi.* 'Camellia' has been tested in a planting at Alapaha Ga., since 1998.

'Camellia' has been asexually propagated on many occasions since 1996 by softwood cuttings at Griffin, Ga. It roots readily from softwood cuttings and in all cases the clones propagated from cuttings have maintained the vegetative and fruit characteristics of the original selection.

'Camellia' has been primarily compared with four southern highbush standard cultivars, 'Georgiagem' (non patented), 'O'Neal' (non patented), 'Sharpblue' (non patented) and 'Star' (PP 10,675). One of the most outstanding characteristics of 'Camellia' is its high degree of plant vigor when grown with and without pine bark mulch. Its plant vigor when grown at Alapaha, Ga. from 1998 to 2000, on a rating scale of 1 to 10 with 10 being excellent, was 6.0 (without mulch) and 9.0 (with mulch) compared to 3.3 and 6.3 for 'Georgiagem', 3.0 and 5.7 for 'O'Neal', 4.3 and 5.7 for 'Sharpblue', and 4.3 and 6.3 for 'Star'.

When grown under field conditions at Alapaha, Ga., from 1999 through 2002, the average berry size, berry color, and plant vigor were outstanding. The 'Camellia' berry size rating of 9.3 was significantly better than 'Georgiagem' (7.5), 'O'Neal' (8.1), 'Sharpblue' (7.7) and 'Star' (7.8). 'Camellia's' berry color rating of 9.0 was significantly better than 'Georgiagem' (7.9), 'O'Neal' (7.9), 'Sharpblue' (8.4) and 'Star' (8.0), and its plant vigor rating of 9.3 was significantly better than 'Geogiagem' (7.0), 'O'Neal' (5.1), 'Sharpblue' (6.8) and 'Star' (6.3). The large berry size and highly blue fruit are very desirable for marketing.

The average 50% flowering date over a 4 year period for 'Camellia' grown under field conditions at Alapaha, Ga., was significantly later than 'O'Neal' (11 days), 'Sharpblue' (15 days), 'Star' (9 days), and similar to 'Georgiagem', thereby reducing the risk of spring freeze damage. Its 50% ripening date was similar to the other four varieties so it is within the mid- to early-season for production.

Some growers in Georgia are growing southern highbush blueberries in a high density system utilizing pine bark beds. A high density planting was established during 2002 at Alapaha, Ga., to evaluate performance of 'Camellia' compared to 'Emerald' (PP 12,165) and 'Star' under these conditions. 'Camellia' showed greater plant vigor (9.3) than 'Emerald' (8.3) or 'Star' (6.5), and greater berry weight (1.92 g) at first harvest and overall harvest (1.48 g) than 'Star' (1.21 g and 1.29 g, respectively) with similar weights to 'Emerald' (1.88 g and 1.75 g, respectively). The total berry yield of 'Emerald' was grater than 'Camellia', but the 15 days earlier flowering date of 'Emerald' greatly increases the risk of substantial frost damage in many years.

BRIEF DESCRIPTION OF THE PHOTOGRAPHS

SUMMARY OF THE INVENTION

Figure 1:
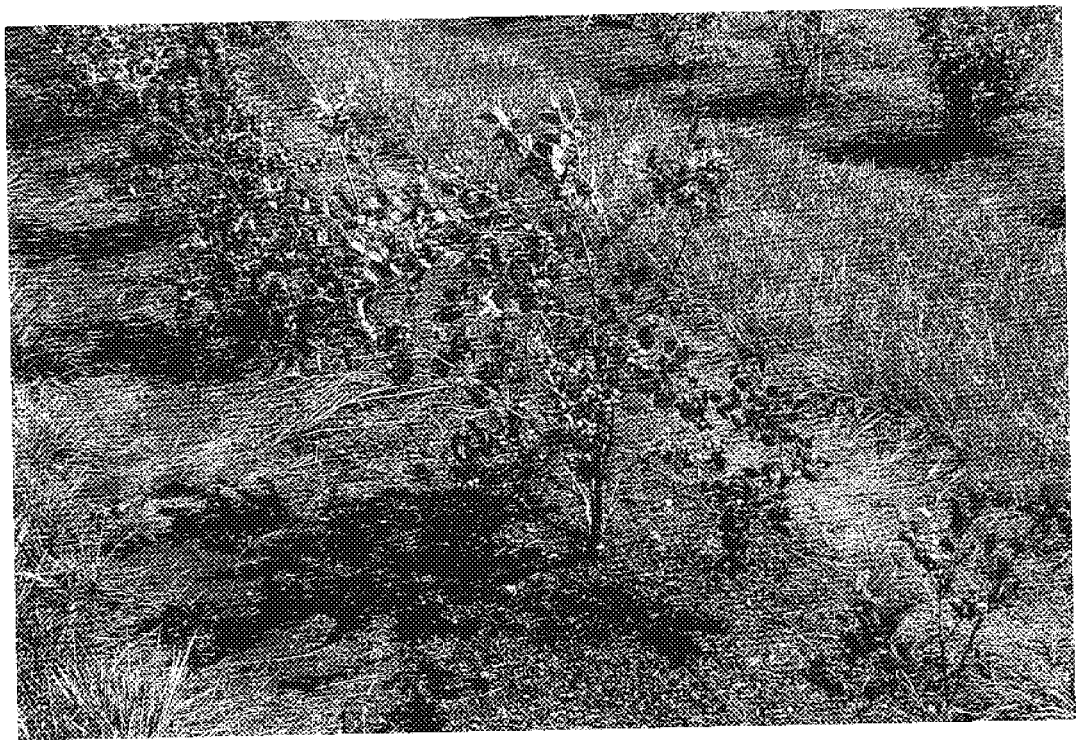
FIG. 1 shows a 2 year old plant bearing fruit at Griffin, Ga. Jun. 13, 2005).
Figure 2:
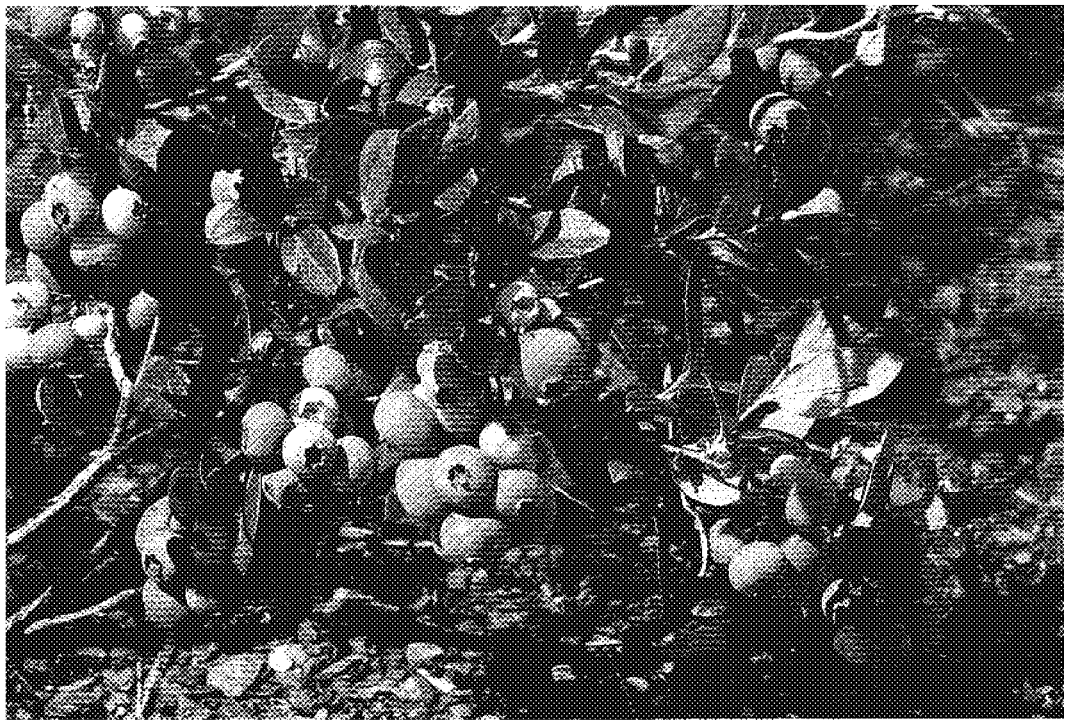
FIG. 2 shows a cluster of berries (Jun. 13, 2005).
Figure 3:
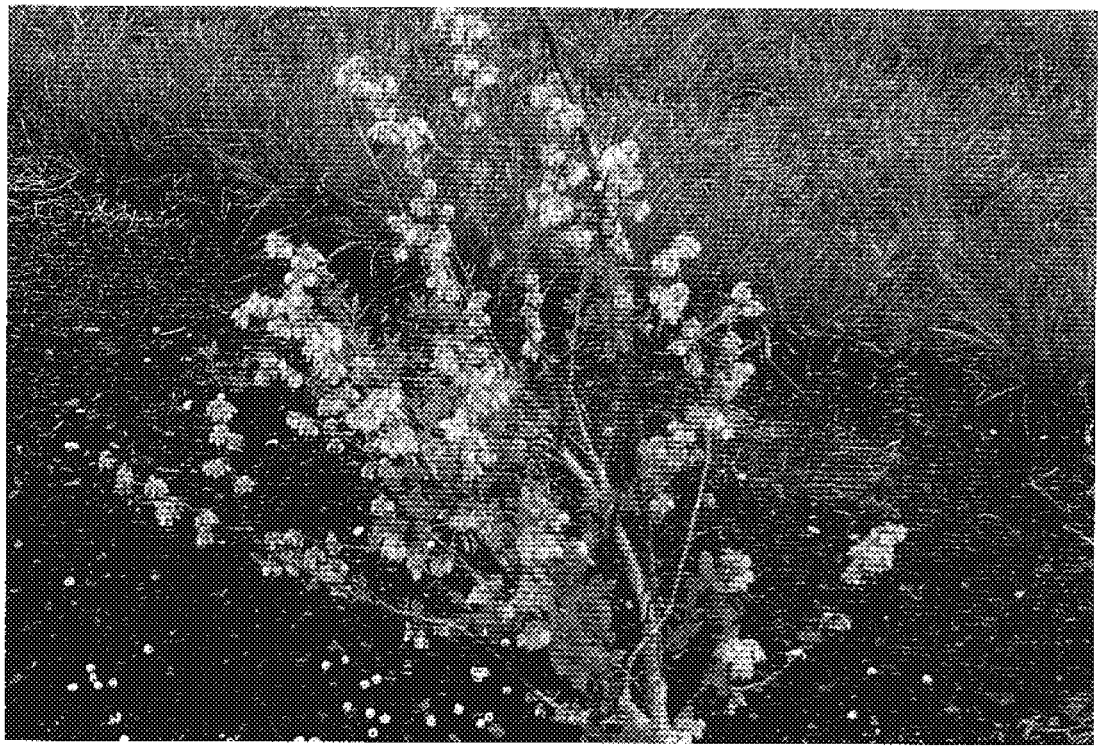
FIG. 3 shows a plant in bloom (Apr. 1, 2005), at Griffin, GA., significantly later than most mid- to early-season varieties.
Figure 4:
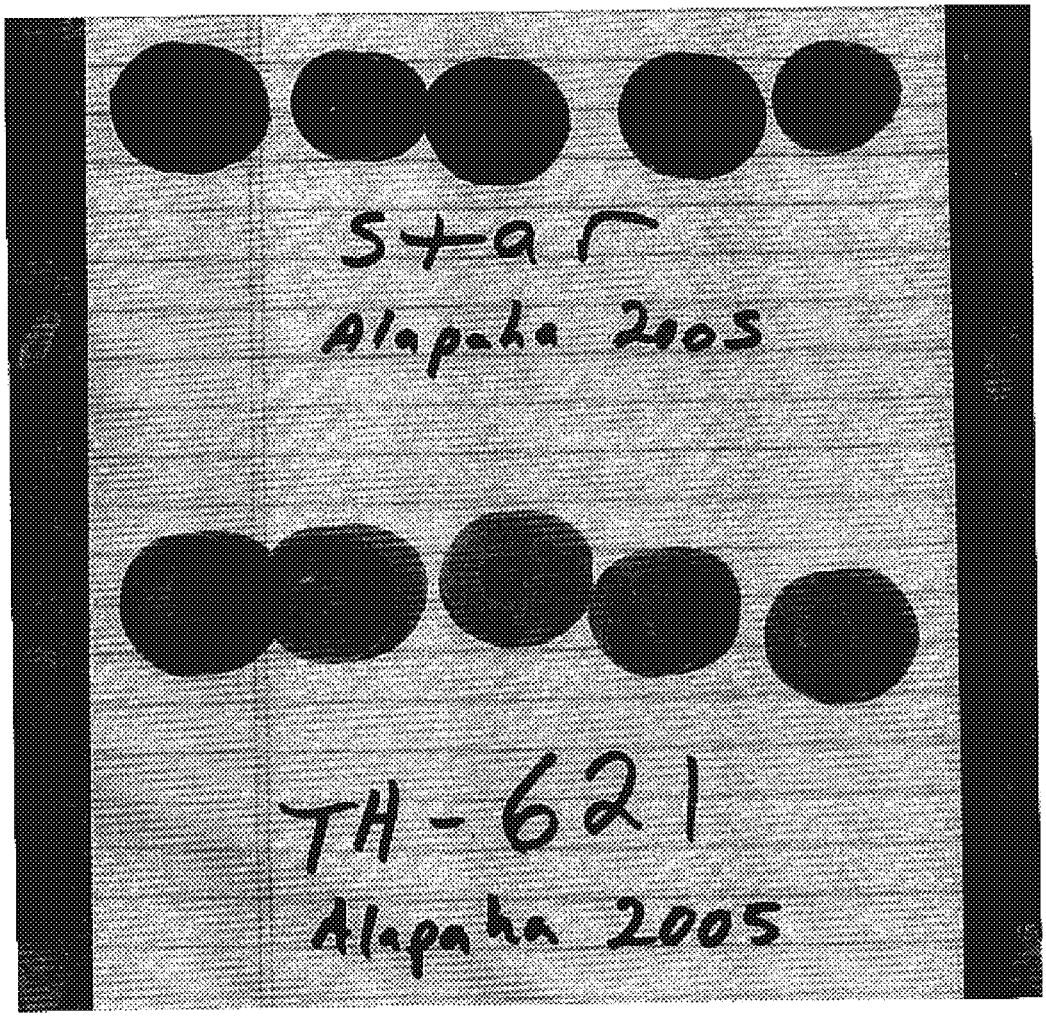
FIG. 4 shows fruit size of 'Camellia' (TH-621) compared to 'Star' (Aug. 11, 2005).

'Camellia' is a mid- to early-season southern highbush blueberry having highly favorable fruit attributes, especially size and color, relatively late flowering, and excellent plant vigor. It has similar chill hour requirements to other early season Southern highbush varieties, in the range of 400 to 450 hours.

BOTANICAL DESCRIPTION OF THE PLANT

The following is a detailed description of the botanical and pomological characteristics of 'Camellia'. Where dimensions, sizes, colors, and other characteristics are given, it is to be understood that such characteristics are approximations and averages set forth as accurately as practicable. Color data are presented in Royal Horticultural Society Colour Chart designations. The descriptions reported herein are largely from specimen plants grown in Alapaha, Ga. and Griffin, Ga., with supplemental irrigation. Plants were 2 to 4 years old.

Plant:

*Size.*—Reaches 1.5 to 2.0 m tall by 4 years. Three to four year old plants have a spread of 20 to 30 cm at the base and 80–110 cm near the top of plant.

*Growth habit.*—Strong upright growth habit. Narrow crowns, limited suckering.

*Growth.*—High vigor; strong cane growth.

*Productivity.*—Medium, averaging 4.5 to 5 lbs per plant each year for 3 to 4 year old plants grown in bark beds with irrigation.

*Cold hardiness.*—Plants should survive in USDA hardiness zones 6 thru 9.

*Chilling requirement.*—Plants require 400 to 450 hours of temperatures at or below 45° F. (7° C.) to induce normal leafing and flowering during the spring.

*Leafing.*—Plants do not readily break numerous leaf buds simultaneously with anthesis.

*Canes.*—Cane 3 years old and older can be 20 to 30 mm in diameter; color is Greyed-Green (197C). 2 years old wood is 5 to 10 mm in diameter; color is Yellow-Green (145A). Current season shoot is 2 to 4 mm in diameter; color is Yellow-Green (145B).

*Diseases.*—Reasonable tolerance to the soil born diseases, pythium, phytophora and rhizoctonia. Less susceptible to septoria leaf spot than 'Star'.

Foliage:

*Leaf color.*—Healthy mature leaves: top side of leaf color is Green (137A), under side of leaf color is Yellow-Green (148C).

*Leaf arrangement.*—Alternate, distichous.

*Leaf shape.*—Elliptic.

*Leaf margins.*—Nearly Entire, slightly crenate near base.

*Leaf venation.*—Reticulate.

*Leaf apices.*—Acuminate.

*Leaf bases.*—Acute to acuminate.

*Leaf dimensions.*—Length 65 to 75 mm; width 25 to 35 mm.

*Leaf surface.*—Smooth, with moderate wax for a highbush cultivar.

*Petioles.*—Small, 4.0 to 6.0 mm long. Color is Yellow-Green (145B). Petiole width is 1.6 to 1.8 mm.

Flowers:

*Date of* 50% *anthesis.*—March 11 (4 year average in southeast Georgia).

*Flower shape.*—Urceolate.

*Flower bud number.*—Medium.

*Flowers per cluster.*—5 to 7.

*Flower fragrance.*—A light, fruit fragrance is sometimes present.

*Corolla color.*—White (155A) open flower.

*Corolla length.*—8.5 to 9.5 mm.

*Corolla width.*—8.5 to 10.0 mm.

*Corolla aperture width.*—3.5 to 4.8 mm.

*Flower peduncle.*—Length 15 to 22 mm; Color Yellow-Green (145A).

*Flower pedicel.*—Length 5 to 8 mm; Color Green (146C).

*Calyx* (*with sepals*).—Diameter 6.5 to 7.0 mm; color Yellow-Green (146D).

*Stamen.*—Length 7.2 to 7.5 mm; number per flower 10; filament color: Yellow-Green (145C).

*Style.*—Length 9.0 to 9.5 mm; color Yellow-Green (145A).

*Pistil.*—Length 11.5 to 12.0 mm; ovary color (exterior) Green (139C).

*Anther.*—Length 4.3 to 4.5 mm; number 10; color Greyed-Orange (165B).

*Pollen.*—Abundance: medium; color Yellow-Orange (18B).

The cultivar has a moderate degree of self-compatibility. It should be grown with another cultivar such as 'Star', 'Palmetto' (PP Application No. 10/909,650, issued on Jul. 4, 2006 as U.S. PP 16,756) or 'O'Neal'.

Fruit:

*Date of* 50% *maturity.*—May 14 (4 year average in southeast Ga.). Date of 10% maturity is May $3^{rd}$ and date of 90% maturity is May $26^{th}$ on average.

*Fruit development period.*—64 to 69 days.

*Berry color.*—With wax Violet-Blue (97C); with wax removed Black (202A).

*Berry surface wax abundance.*—Very high.

*Berry flesh color.*—White (155C).

*Berry weight.*—1st harvest 2.3 g to 2.6 g; $2^{nd}$ harvest 1.8 g to 2.0 g.

*Berry size.*—Height from calyx to scar 14.0 to 15.0 mm; diameter 18.0 to 21.0 mm.

*Berry shape.*—Berry shape is nearly spherical.

*Fruit stem scar.*—Medium, dry, no tearing.

*Berry firmness.*—Good to excellent.

*Berry flavor and texture.*—Good flavor, excellent texture.

*Storage quality.*—Good to excellent.

*Suitability for mechanical harvesting.*—Not likely.

*Uses.*—Primarily used as fresh fruit for shipping.

Seed:

*Seed abundance in fruit.*—Low to medium.

*Seed color*—Greyed-Orange (165B).

*Seed dry weight.*—51.2 mg per 100 seed.

*Seed size.*—1.0 to 1.5 mm long for fully developed seeds.

We claim:

1. A new and distinct variety of southern highbush blueberry plant, substantially as illustrated and described.

* * * * *